United States Patent
Williams

(10) Patent No.: US 11,085,047 B2
(45) Date of Patent: Aug. 10, 2021

(54) SYNTHETIC CANNABINOID COMPOUNDS FOR TREATMENT OF SUBSTANCE ADDICTION AND OTHER DISORDERS

(71) Applicant: MyMD Pharmaceuticals (Florida), Inc., Tampa, FL (US)

(72) Inventor: Jonnie R. Williams, Sarasota, FL (US)

(73) Assignee: MyMD Pharmaceuticals (Florida), Inc., Tampa, FL (US)

( * ) Notice: Subject to any disclaimer, the term of this patent is extended or adjusted under 35 U.S.C. 154(b) by 0 days.

(21) Appl. No.: 16/612,472

(22) PCT Filed: Feb. 11, 2019

(86) PCT No.: PCT/US2019/017433
§ 371 (c)(1),
(2) Date: Nov. 11, 2019

(87) PCT Pub. No.: WO2019/164689
PCT Pub. Date: Aug. 29, 2019

(65) Prior Publication Data
US 2020/0061138 A1    Feb. 27, 2020

Related U.S. Application Data

(60) Provisional application No. 62/632,448, filed on Feb. 20, 2018.

(51) Int. Cl.
| | | |
|---|---|---|
| *C07C 39/23* | (2006.01) | |
| *C07D 311/00* | (2006.01) | |
| *A61K 31/00* | (2006.01) | |
| *C12N 15/00* | (2006.01) | |
| *C12N 15/82* | (2006.01) | |
| *A61K 31/352* | (2006.01) | |
| *A61K 36/185* | (2006.01) | |

(52) U.S. Cl.
CPC ........ *C12N 15/8243* (2013.01); *A61K 31/352* (2013.01); *A61K 36/185* (2013.01); *C12N 15/8257* (2013.01)

(58) Field of Classification Search
CPC .. A61K 31/352; C07C 2601/10; C07C 39/23; C07D 311/78; A01H 6/28
See application file for complete search history.

(56) References Cited

U.S. PATENT DOCUMENTS

| | | | | |
|---|---|---|---|---|
| 8,337,908 B2* | 12/2012 | Letzel | ............. | A61Q 19/00 |
| | | | | 424/725 |
| 10,059,683 B2* | 8/2018 | Dialer | ............. | C07D 311/80 |
| 2016/0000843 A1 | 1/2016 | Lowe et al. | | |
| 2017/0211049 A1 | 7/2017 | Page et al. | | |

FOREIGN PATENT DOCUMENTS

| | | | |
|---|---|---|---|
| CA | 2957953 | A1 | 12/2015 |
| WO | 2011/017798 | A1 | 2/2011 |
| WO | 2016/004121 | A1 | 1/2016 |
| WO | 2016/127111 | A1 | 8/2016 |
| WO | 2016/189384 | A1 | 12/2016 |
| WO | 2017/011210 | A1 | 1/2017 |

OTHER PUBLICATIONS

Maa. E and Figi, P. Epilepsia, (2014) 55(6):783-786. (Year: 2014).*
Aizpurua-Olaizola et al, Journal of Natural Products, Evolution of the Cannabinoid and Terpene Content during the Growth of *Cannabis sativa* Plants from Different Chemotypes , 2016, pp. 324-325. (Year: 2016).*
Mazzocanti et al, ChemComm, Cannabis through the looking glass: chemo- and enantio-selective separation of phytocannabinoids by enantioselective ultra high performance supercritical fluid chromatography, 2017, 53, pp. 12262-12265. (Year: 2017).*
Apr. 11, 2019—(WO) International Search Report and Written Opinion—App PCT/US2019/017433.
Jan. 26, 2021—(JP) Notice of Reason for Refusal—App. No. 2020-553539.
Taglialatela-Scafati, O. et al., "Cannabimovone, a Cannabinoid with a Rearranged Terpenoid Skeleton from Hemp," Eur. J. Org. Chem., pp. 2067-2072 (2010).
Taura, F. et al., "Cannabidiolic-acid synthase, the chemotype-determining enzyme in the fiber-type *Cannabis sativa*," FEBS Letters, vol. 581, pp. 2929-2934 (2007).
Feb. 3, 2021—(CN) First Office Action—App 201980014261.X.
Mar. 3, 2021—(CA)—Second Examiner's Report—App 3,091,776.
Mar. 12, 2021—(EP) Extended European Search Report—App 19756525.2.

* cited by examiner

*Primary Examiner* — Sikarl A Witherspoon
(74) *Attorney, Agent, or Firm* — Banner & Witcoff, Ltd.

(57) ABSTRACT

A method of increasing the cannabinoid levels in a genetically modified *Cannabis sativa* plant includes genetically modifying the plant to induce the overexpression of the gene that controls the expression of tetrahydrocannabinolic acid (THCA) synthase and/or cannabidiolic acid (CBDA) synthase. The overexpression of THCA synthase and CBDA synthase catalyzes an increased synthesis of cannabigerolic acid to tetrahydrocannabinolic acid and cannabidiolic acid, as well as the cannabinoids (3aR)-2,4,4-trimethyl-7-pentyl-3,3a,4,9b-tetrahydrocyclopenta[c]chromen-9-ol and 2-((1R, 5R)-3-methyl-5-(prop-1-en-2-yl)cyclopent-2-en-1-yl)-5-pentylbenzene-1,3-diol. Pharmaceutical compositions comprising the modified cannabinoids produced by the transgenic *Cannabis sativa* plant or prepared synthetically are used to treat various diseases and conditions.

6 Claims, 1 Drawing Sheet

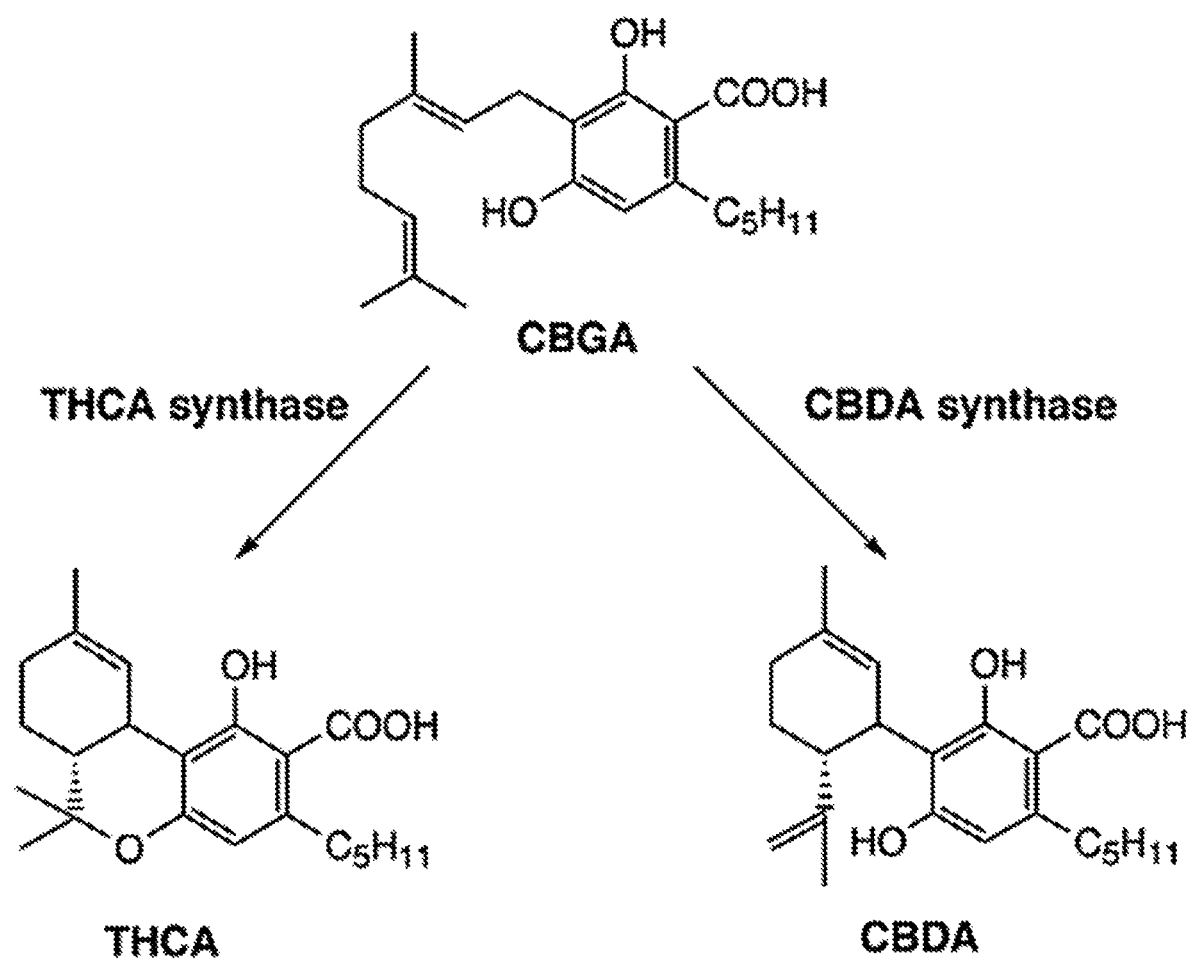

SYNTHETIC CANNABINOID COMPOUNDS FOR TREATMENT OF SUBSTANCE ADDICTION AND OTHER DISORDERS

CROSS-REFERENCE TO RELATED APPLICATION

This application is a U.S. National Phase under 35 U.S.C. § 371 of International Application No. PCT/US2019/017433 (published as WO 2019/164689 A1), filed Feb. 11, 2019, which claims priority to U.S. Provisional Application No. 62/632,448, filed Feb. 20, 2018. Benefit of the filing date of each of these prior applications is hereby claimed. Each of these prior applications is hereby incorporated by reference in its entirety.

BACKGROUND

There has been considerable research in recent years on the therapeutic effects of *cannabis* including its constituents tetrahydrocannabinol (THC) and cannabidiol (CBD). There remains a need for improved compounds for treating indications such as depression, substance addiction, smoking cessation, pain, cancers, autoimmune disorders, and/or disorders associated with chronic inflammation. The compounds described herein may be harvested from a genetically modified *Cannabis sativa* plant or the compounds described herein may be prepared synthetically.

SUMMARY

In accordance with aspects disclosed herein, methods of increasing the cannabinoid levels in genetically modified *Cannabis sativa* plants are disclosed. In other aspects, methods are disclosed of genetically modifying a *Cannabis sativa* plant by genetically modifying the plant to induce the overexpression of the gene that controls the expression of tetrahydrocannabinolic acid (THCA) synthase. In one aspect, the overexpression of THCA synthase catalyzes an increased synthesis of cannabigerolic acid to tetrahydrocannabinolic acid. In still other aspects, the tetrahydrocannabinolic acid in the genetically modified *Cannabis sativa* plant is convened into increased levels of cannabinoids in the plant. In one aspect, the cannabinoid is (3aR)-2,4,4-trimethyl-7-pentyl-3,3a,4,9b-tetrahydrocyclopenta[c]chromen-9-ol. According to another aspect, the genetically modified *Cannabis sativa* plant includes a genetic modification that induces the *Cannabis sativa* plant to overexpress the gene controlling the expression of cannabidiolic acid (CBDA) synthase. The CBDA synthase catalyzes an increased synthesis of cannabigerolic acid to cannabidiolic acid, and the cannabidiolic acid is converted into an increased cannabinoid level in the plant.

In one aspect, methods of genetically modifying a *Cannabis sativa* plant to produce increased levels of cannabinoids are disclosed. In another aspect, a *Cannabis sativa* plant is genetically modified to include a genetic modification that induces the plant to overexpress the gene controlling the expression of cannabidiolic acid (CBDA) synthase and the CBDA synthase catalyzes an increased synthesis of cannabigerolic acid to cannabidiolic acid. In other aspects, the cannabidiolic acid in the genetically modified *Cannabis sativa* plant is converted into increased levels of cannabinoids in the plant. In another aspect, the cannabinoid is 2-((1R,5R)-3-methyl-5-(prop-1-en-2-yl)cyclopent-2-en-1-yl)-5-pentylbenzene-1,3-diol. According to another aspect, the genetically modified *Cannabis sativa* plant includes a second genetic modification that induces the *Cannabis sativa* plant to overexpress the gene controlling the expression of THCA synthase that catalyzes an increased synthesis of cannabigerolic acid to tetrahydrocannabinolic acid, and the tetrahydrocannabinolic acid is converted into a second increased cannabinoid level in the plant.

In accordance with another aspect, a transgenic *Cannabis sativa* plant is disclosed that produces increased levels of cannabinoid compounds. In one aspect, the cannabinoid compound is (3aR)-2,4,4-trimethyl-7-pentyl-3,3a,4,9b-tetrahydrocyclopenta[c]chromen-9-ol. In another aspect, the cannabinoid compound is 2-((1R,5R)-3-methyl-5-(prop-1-en-2-yl)cyclopent-2-en-1-yl)-5-pentylbenzene-1,3-diol.

In other aspects, a method of increasing the cannabinoid levels in a *Cannabis sativa* plant is disclosed in which the plant includes a genetic modification that induces the plant to overexpress a gene controlling the catalyzation of the synthesis of cannabigerolic acid, and the increased level of cannabigerolic acid is synthesized into cannabinoids in the plant.

In one aspect, the modified cannabinoid compound (3aR)-2,4,4-trimethyl-7-pentyl-3,3a,4,9b-tetrahydrocyclopenta[c]chromen-9-ol or a pharmaceutically acceptable salt thereof is disclosed. In another aspect, a modified cannabinoid compound is 2-((1R,5R)-3-methyl-5-(prop-1-en-2-yl)cyclopent-2-en-1-yl)-5-pentylbenzene-1,3-diol or a pharmaceutically acceptable salt thereof.

In another aspect, a composition comprises a therapeutically effective dose of a modified cannabinoid compound or a pharmaceutically acceptable salt thereof and a pharmaceutically acceptable vehicle therefor.

BRIEF DESCRIPTION OF THE DRAWINGS

A more complete understanding of the present invention and certain advantages thereof may be acquired by referring to the following detailed description in consideration with the accompanying drawings, in which:

The FIGURE shows the biosynthetic pathway of cannabinoid synthesis in the *Cannabis sativa* plant. THCA synthase and CBDA synthase catalyze oxidative cyclization of the monoterpene moiety of cannabigerolic acid (CBGA) to form THCA and CBDA. Various cannabinoid compounds and cannabinoid derivatives are generated from the THCA and CBDA. Two of the most well-known cannabinoids, THC and CBD, are generated from THCA and CBDA by non-enzymatic decarboxylation during smoking and storage.

DETAILED DESCRIPTION

Cannabinoids produced by the *Cannabis sativa* plant have the potential to provide new therapeutic compounds to treat a vast assortment of diseases and other human ailments. More than 100 different cannabinoids have been isolated from *cannabis* and each cannabinoid compound exhibits various effects. For example, THC is well-known for its psychological effects and CBD is known for its non-psychoactive effects. THC and related derivatives typically exert therapeutic activities via cannabinoid receptors found in humans and other mammals. CBD is an isomer of THC. CBD and CBD derivatives also exhibit anti-oxidative and anti-inflammatory effects through pathways not related to cannabinoid receptors. Cannabinoid type 1 ($CB_1$) receptors are found primarily in the brain, including the basal ganglia and in the limbic system, and the hippocampus and the striatum, as well as the cerebellum. $CB_1$ receptors can be found in the human anterior eye and retina. Research indicates that cannabinoid type 2 ($CB_2$) receptors are responsible for anti-inflammatory and other therapeutic effects related to cannabinoids.

Cannabis plants that contain high levels of cannabinoids such as THC, for example, are typically known as "marijuana" plants. Cannabis plants with a low cannabinoid content are categorized as "hemp" plants. Individual countries usually determine the levels of cannabinoids that differentiate between cannabis plants that are categorized as marijuana or hemp plants. Generally, the THC content on a dry-weight basis for a cannabis plant categorized as a hemp plant is 0.3% or less. *Cannabis sativa* plants having THC, CBD, and other cannabinoid content levels greater than 0.3% are typically considered marijuana plants. Medical marijuana typically contains cannabinoid levels between 5 and 20%. Other *Cannabis sativa* plants may produce cannabinoid levels from 25 to 30%. In one aspect, a genetically modified *Cannabis sativa* plant is disclosed herein that produces an increased level of cannabinoids that is at least 20%. In another aspect, a genetically modified *Cannabis sativa* plant is disclosed herein that produces an increased level of cannabinoids that is about 5 to 20%. In yet another aspect, a genetically modified *Cannabis sativa* plant is disclosed herein that produces an increased level of cannabinoids that is about 25 to 30%. In one aspect, the non-genetically modified *Cannabis sativa* plant is classified as a hemp plant. In another aspect, the non-genetically modified *Cannabis sativa* plant is classified as a marijuana plant. In other aspects, the cannabinoid is a THC derivative. In other aspects, the cannabinoid is (3aR)-2,4,4-trimethyl-7-pentyl-3,3a,4,9b-tetrahydrocyclopenta[c]chromen-9-ol. In other aspects, the cannabinoid is a cannabidiol or cannabidiol derivative. In yet another aspect, the cannabinoid is 2-((1R,5R)-3-methyl-5-(prop-1-en-2-yl)cyclopent-2-en-1-yl)-5-pentyl benzene-1,3-diol.

The *Cannabis sativa* plant materials that contain cannabinoids may include the plant or plant part such as the bark, leaves, stem, root, wood, flowers, fruits, seeds, berries, exudates, extracts, or combinations thereof. As used herein, a *Cannabis sativa* plant includes variants, subspecies, chemovars, genetic crosses, self-crosses, or hybrids. In accordance with one aspect disclosed herein, a transgenic *Cannabis sativa* plant is genetically modified to express, repress, alter, or mutate a gene or genes involved in the cannabinoid biosynthesis pathway. According to yet another aspect, a genetically modified *Cannabis sativa* plant disclosed herein may produce increased levels of cannabinoids due to a modified gene or genes encoding an enzyme(s) or protein(s) involved in the biosynthesis of the various cannabinoids.

The biosynthetic pathway of the *Cannabis sativa* plant that produces the various cannabinoids starts with the precursor cannabigerolic acid. As shown in the FIGURE, the enzymes THCA synthase and CBDA synthase catalyze the biosynthesis of cannabigerolic acid to tetrahydrocannabinol acid (THCA) and cannabidiol acid (CBDA), respectively, as well as other cannabinoids. It is known that various other cannabinoids are produced via this pathway. THC, CBD, and other cannabinoid derivatives are generated artificially from THCA and CBDA by non-enzymatic decarboxylation. Evolution of the Cannabinoid and Terpene Content during the Growth of *Cannabis sativa* Plants from Different Chemotypes, Oier Aizpurua-Olaizola, Umut Soydaner, Ekin Öztiirk, Daniele Schibano, Yilmaz Simsir, Patricia Navarro, Nestor Etxebarria, and Aresatz Usobiaga, Journal of Natural Products 2016 79 (2), 324-331. Various classes of cannabinoids are biosynthesized via this general pathway to include THC (tetrahydrocannabinol), THCA (tetrahydrocannabinolic acid), CBD (cannabidiol), CBDA (cannabidiolic Acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

A genetic engineering technique to increase the cannabinoid content in a *Cannabis sativa* plant involves manipulating the gene controlling the expression of tetrahydrocannabinolic acid (THCA) synthase and/or manipulating the gene controlling the expression of controlling the expression of a cannabidiolic acid (CBDA) synthase. In one aspect, the overexpression of the gene that produces THCA synthase results in increased levels of THCA synthase in the *Cannabis sativa* plant. The Gene Controlling Marijuana Psychoactivity: Molecular Cloning and Heterologous Expression of Delta1-Tetrahydrocannabinolic Acid Synthase from *Cannabis sativa* L. J. Biol. Chem. 2004 279: 39767. As shown in the FIGURE, the THCA synthase catalyzes the synthesis of cannabigerolic acid (CBGA) to tetrahydrocannabinolic acid (THCA). The increased expression of THCA synthase thus catalyzes increased levels of CBGA to THCA. THCA is subsequently converted or synthesized into other THC related cannabinoids. In another aspect, the overexpression of the gene that produces CBDA synthase results in increased levels of CBDA synthase in the *Cannabis sativa* plant. Taura Futoshi, Sirikantaramas Supaart, Shoyama Yoshinari, Yoshikai, Kazuyoshi, Shoyama Yukihiro, and Morimoto Satoshi (2007), Cannabidiolic-acid synthase, the chemotype-determining enzyme in the fiber-type *Cannabis sativa*, FEBS Letters, 581. As shown in the FIGURE, the CBDA synthase catalyzes the synthesis of cannabigerolic acid (CBGA) to cannabidiolic acid (CBDA). CBDA is subsequently converted or synthesized into other CBD related cannabinoids. The increased expression of CBDA synthase thus catalyzes increased levels of CBGA to CBDA. According to the genetic engineering technique disclosed herein, increased levels of (3aR)-2,4,4-trimethyl-7-pentyl-3,3a,4,9b-tetrahydrocyclopenta[c] chromen-9-ol and 2-((1R, 5R)-3-methyl-5-(prop-1-en-2-yl)cyclopent-2-en-1-yl)-5-pentyl benzene-1,3-diol can be generated from transgenic *Cannabis sativa* plants.

According to one aspect, the genetically modified *Cannabis sativa* plants disclosed herein may produce cannabinoid content levels on a dry weight-weight basis of, for example, at least, greater than, less than, equal to, or any number in between about 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 2.00%, 3.00%, 4.00%, 5.00%, 6.00%, 6.00%, 7.00%, 7.00%, 8.00%, 9.00%, 10.00%, 11.00%, 12.00%, 13.00%, 14.00%, 15.00%, 16.00%, 17.00%, 18.00%, 19.00%, 20.00%, 21.00%, 22.00%, 23.00%, 24.00%, 25.00%, 26.00%, 27.00%, 28.00%, 29.00%, 30.00%, 31.00%, 32.00%, 33.00%, 34.00%, 35.00%, 36.00%, 37.00%, 38.00%, 39.00%, 40.00%, 41.00%, 42.00%, 43.00%, 44.00%, 45.00%, 46.00%, 47.00%, 48.00%, 49.00%, 50.00%.

As used herein, the terms "enzyme," "protein," "polypeptide," and "peptide" are used interchangeably herein to designate a series of amino acid residues, connected to each other by peptide bonds between the alpha-amino and carboxy groups of adjacent residues. The terms "enzyme," "protein," "peptide," and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "enzyme," "protein," and "peptide" are used interchangeably herein when referring to a gene product and fragments thereof. Thus, exemplary enzymes, polypeptides, peptides, or proteins include gene products, naturally occurring enzymes, proteins, homologs, orthologs, paralogs, fragments and other equivalents, variants, fragments, and analogs of the foregoing.

According to one aspect, genes encoding a polypeptide related to cannabinoid biosynthesis may be utilized to overexpress or inhibit the expression of the polypeptide in a *Cannabis sativa* plant in which the polypeptide may normally be found. In other aspects, the gene may be used to design a polynucleotide that inhibits or induces the expression of the gene, and the polynucleotide may be introduced into a cell of the *Cannabis sativa* plant.

An "amino acid sequence" may be determined directly for an enzyme, protein or peptide, or inferred from the corresponding nucleic acid sequence. A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA. "Heterologous" as applied to nucleic acids is of different origin than that of the natural cannabis plant cell.

A "vector" refers to a piece of DNA, either single or double stranded. The vector can be for example, of plasmid or viral origin, which typically encodes a selectable or screenable marker or transgenes. The vector is used to transport the foreign or heterologous DNA into a suitable host cell. Once in the host cell, the vector can replicate independently of or coincidental with the host chromosomal DNA. Alternatively, the vector can target insertion of the foreign or heterologous DNA into a host chromosome.

The term "transgenic" refers to cannabis plants or plant cells that have been "transformed." "Transformed" describes the introduction of DNA into the cannabis plant or plant cell. In most cases, the DNA is introduced into the cannabis plant or plant cell in the form of a vector containing the DNA segment. A transformed *Cannabis sativa* plant may be identified by selectable markers and report genes in accordance with methods known in the art. "Expressed" describes a protein that is produced in a plant cell when its DNA is transcribed to mRNA that is translated to the protein. "Inhibition" describes a measurable decrease in the cellular level of mRNA transcribed from the gene (i.e., coding polynucleotide), and/or in the cellular level of a peptide, polypeptide, or protein product of the coding polynucleotide. "Overexpression" describes a greater expression level of a gene in a cannabis plant or cell compared to the expression in a wild-type cannabis plant or cell. "Suppressed" refers to decreased expression or activity of a protein.

The term "% sequence identity" describes the extent to which the sequences of DNA or protein segments are invariant throughout a window of alignment of sequences such as nucleotide sequences or amino acid sequences and is determined by comparing two optimally aligned sequences over a comparison window. An identity fraction for a sequence aligned with a reference sequence is the number of identical components that are shared by the sequences, divided by the length of the alignment not including gaps introduced by the alignment algorithm. "% identity" is the identity fraction times 100. "Substantially identical" describes nucleotide sequences that are more than 85% identical to a reference sequence.

"Promoter" describes a regulatory DNA that initializes transcription. Using methods known to a person of ordinary skill in the art, recombinant DNA constructs are assembled and usually include a promoter operably linked to DNA.

Definitions of common terms in cell biology and molecular biology can be found in The Encyclopedia of Molecular Biology, published by Blackwell Science Ltd., (1994) (ISBN 0-632-02182-9); Benjamin Lewin, (2009) Genes X, published by Jones & Bartlett Publishing, (ISBN-10: 0763766321); Kendrew et al. (eds.) (1995), Molecular Biology and Biotechnology: a Comprehensive Desk Reference, published by VCH Publishers, Inc., (ISBN 1-56081-569-8) and Current Protocols in Protein Sciences (2009), Wiley Intersciences, Coligan et al., eds.

Unless otherwise stated, the present disclosure is performed using standard procedures, as described, for example in Sambrook et al., (2001) Molecular Cloning: A Laboratory Manual (3 ed.), Cold Spring Harbor Laboratory Press, Cold Spring Harbor, N.Y., USA; Davis et al., (1995) Basic Methods in Molecular Biology. Elsevier Science Publishing, Inc., New York, USA; or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons. Inc.), which are all incorporated by reference herein in their entireties.

In some embodiments, *Cannabis sativa* plant genes encoding a polypeptide, related to the biosynthesis of THCA or CBDA, may be utilized to overexpress or inhibit the expression of the polypeptide in the *Cannabis sativa* plant in which the polypeptide is normally found. For example, the gene or a related vector may be introduced into a cell of the plant in a genetic locus where the gene is not normally found, or a native copy of the gene or related vector may be placed under regulatory control elements that lead to increased expression of the native gene or vector. In other examples, the gene may be used to design a polynucleotide that inhibits the expression of the gene, and the polynucleotide may be introduced into a cell of the cannabis plant. Accordingly, genetically modified *Cannabis sativa* plants may be engineered to increase or decrease the levels of certain cannabinoids synthesized, such as (3aR)-2,4,4-trimethyl-7-pentyl-3.3a,4.9b-tetrahydrocyclopenta[c] chromen-9-ol and 2-((1R,5R)-3-methyl-5-(prop-1-en-2-yl)cyclopent-2-en-1-yl)-5-pentyl benzene-1,3-diol, by overexpressing or inhibiting one or several key genes related to cannabinoid biosynthesis.

In one example, a transgenic *Cannabis sativa* plant may be cultivated with increased levels of (3aR)-2,4,4-trimethyl-7-pentyl-3,3a,4.9b-tetrahydrocyclopenta[c] chromen-9-ol and/or 2-((1R,5R)-3-methyl-5-(prop-1-en-2-yl)cyclopent-2-en-1-yl)-5-pentyl benzene-1,3-diol, by exposing a the *Cannabis sativa* plant or cell to a vector or exogenous DNA construct that includes a promoter that is operable in the Cannabis sativa plant or cell and a DNA sequence capable of encoding an enzyme(s) or protein(s) critical to the cannabinoid biosynthesis pathway thereby inducing increased levels of (3aR)-2,4,4-trimethyl-7-pentyl-3,3a,4,9b-tetrahydrocyclopenta[c] chromen-9-ol and/or 2-((1R,5R)-3-methyl-5-(prop-1-en-2-yl)cyclopent-2-en-1-yl)-5-pentyl benzene-1,3-diol production and biosynthesis. In one example, the target enzyme is THCA synthase and/or CBDA synthase. Accordingly, the *Cannabis sativa* plant is transformed by the DNA construct or vector. The transformed plant or cells are selected and the resulting transgenic *Cannabis sativa* plant is regenerated using conventional techniques.

The expression of isolated nucleic acids encoding an enzyme or protein involved in the cannabinoid biosynthesis pathway can be achieved by operably linking the DNA or cDNA to a promoter, and then incorporated into an expression vector. Vectors can be suitable for replication and integration in either prokaryotes or eukaryotes. Typical expression vectors contain transcription and translation terminators, initiation sequences, and promoters that regulate the expression of the DNA encoding an enzyme or protein involved in the cannabinoid biosynthesis pathway. The vector is then introduced into the appropriate host cell.

In accordance with one aspect of the current disclosure, a genetically modified Cannabis sativa plant includes a *Cannabis sativa* plant transformation vector comprising a nucleic acid encoding a polypeptide having at least 80%, 85%, 88%, 90%, 92%, 95%, 98%, 99%, or 100% sequence identity to a *Cannabis sativa* plant gene related to enzymes (e.g., THCA synthase. CBDA synthase, etc.), proteins, or other components critical to the cannabinoid biosynthesis pathway, or directly related to the biosynthesis and/or the metabolic pathway generating the cannabinoid compounds (3aR)-2,4,4-trimethyl-7-pentyl-3.3a,4.9b-tetrahydrocyclopenta[c] chromen-9-ol and/or 2-((1R,5R)-3-methyl-5-(prop-1-en-2-yl)cyclopent-2-en-1-yl)-5-pentyl benzene-1,3-diol. In accordance with another aspect, the nucleic acid is operably linked to a promoter. In accordance with another aspect, a nucleic acid construct for a genetically modified *Cannabis sativa* plant is provided. The nucleic acid construct comprises a polynucleotide sequence encoding a polypeptide having at least 80% sequence identity to a *Cannabis sativa* plant gene related to the cannabinoid and cannabinoid derivatives biosynthesis pathway, and one or more control sequences for driving expression of the polynucleotide sequence in the genetically modified *Cannabis sativa* plant.

The compound 2-((1R,5R)-3-methyl-5-(prop-1-en-2-yl) cyclopent-2-en-1-yl)-5-pentyl benzene-1,3-diol has the structure:

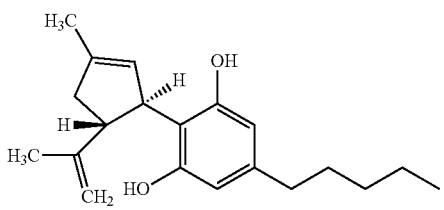 [SMILES: C=C(C)[C@@H]1CC(C)=C[C@H]1c1c(O)cc(CCCCC)cc1O]

The compound (3aR)-2,4,4-trimethyl-7-pentyl-3,3a,4,9b-tetrahydrocyclopenta[c]chromen-9-ol has the structure:

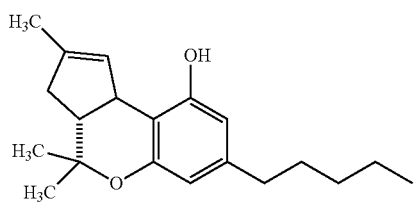

According to one aspect, the cannabinoid compounds described herein may be formed as salts, which may be helpful to improve chemical purity, stability, solubility, and/or bioavailability. Non-limiting examples of possible salts are described in P. H. Stahl et al., Handbook of Pharmaceutical Salts: Properties. Selection and Use, Weinheim/Zilrich: Wiley-VCH/VHCA, 2002, including salts of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

Compounds described herein may be harvested from the genetically modified Cannabis sativa plant previously described. The compounds described herein may also be prepared synthetically using known techniques with appropriate modifications to the reactants to form the structures shown herein or by other suitable pathways that will be apparent to persons skilled in the art. By way of non-limiting example, compounds described herein may be synthesized according to one or more of the following pathways described in Razdan, Total Synthesis of Cannabinoids, SISA Incorporated, Cambridge, Mass., such as the THC synthesis described at p. 201 or the CBD synthesis described at p. 224, with appropriate modifications to the reactants, as will be apparent to persons skilled in the art, to yield the structures disclosed herein.

Compounds intended for administration to humans or other mammals generally should have very high purity. In the case of synthetically prepared compounds, purity refers to the ratio of a compound's mass to the total sample mass following any purification steps. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

Compounds described herein that exist in more than one optical isomer form (enantiomers) may be provided either as racemic mixture or by isolating one of the enantiomers, the latter case in which purity as described above may refer to enantiomeric purity.

As described above, cannabinoids and related cannabinoid derivatives typically exert therapeutic and anti-inflammatory activities via $CB_1$ and $CB_2$ receptors. While not wanting to be bound by theory, compounds disclosed herein may also exhibit properties as inhibitors of monoamine oxidase (MAO) activity, including either or both of MAO-A and MAO-B activity. These properties may enable compounds to be effective for treating indications associated with MAO activity, such as depression, pain, substance addiction, smoking cessation, and the like. Compounds disclosed herein also (or alternatively) may exhibit anti-inflammatory properties owing to the compound's interaction with inflammation pathways, including by way of example, interleukins such as IL-1 and IL-6, TNF, cyclooxygenase (COX), and the like. A compound's ability to inhibit MAO-A and/or MAO-B activity, and/or its ability to inhibit COX and/or other pathways associated with inflammation may be evaluated using assays well known to persons of ordinary skill in the art.

Hydrogen peroxide ($H_2O_2$) is a stable, uncharged and freely diffusible reactive oxygen species (ROS) and second messenger. The generation of $H_2O_2$ in the brain is especially high because of the high oxygen consumption in the tissue. ROS are essentially produced by mitochondria, and the ability to block mitochondrial enzymes such as MAO may prevent early stage $H_2O_2$ production. In some examples, the compounds disclosed herein may specifically target $H_2O_2$, such as by inhibiting the synthesis of $H_2O_2$, thereby modulating $H_2O_2$ levels to treat a variety of disorders associated with elevated levels of $H_2O_2$.

In some aspects, a modified cannabinoid compound as described herein is administered to an individual in need thereof for the treatment of a substance addiction, such as alcohol, tobacco, opioid, prescription drugs, cocaine, benzodiazepines, amphetamines, hallucinogens, inhalants, phencyclidine, or other drug addictions. Such treatments also are inclusive of treating withdrawal in dependency on benzodiazepines, opiates, or alcohol, as well as symptoms experienced by patients with substance use disorders, such as anxiety, mood symptoms, pain, and insomnia.

In addition to anxiety that is associated with substance use disorders, the modified cannabinoid compounds may be effective for treating other types of anxiety disorders, such as post-traumatic stress disorder, general anxiety disorder, panic disorder, social anxiety disorder, and obsessive-compulsive disorder.

In other aspects, a modified cannabinoid compound as described herein may be administered to an individual in need thereof for the treatment of multiple sclerosis, fibromyalgia, epilepsy or neuropsychiatric disorders that are linked to epilepsy, such as neurodegeneration, neuronal injury, and psychiatric diseases. The modified cannabinoid compounds may be effective for potentiating the anticonvulsant activity of other active agents such as phenytoin and diazepam.

In still other aspects, a modified cannabinoid compound as described herein may be used in as an antipsychotic for treating patients with schizophrenia. The modified cannabinoid compounds also may be effective to reduce intraocular pressure, such as in the treatment of glaucoma.

In yet other aspects, a modified cannabinoid compound as described herein may be administered to an individual in need thereof for the treatment of cancer. The modified cannabinoid compound may be effective to block cancer cells from spreading around the body and invading an area entirely; for suppressing the growth of cancer cells and/or promoting the death of cancer cells.

The modified cannabinoid compounds as described herein may be useful in the treatment of Type 1 diabetes, which is caused by inflammation when the immune system attacks cells in the pancreas; as well as acne, which is caused, in part, by inflammation and overworked sebaceous glands on the body. The anti-inflammatory properties of the compounds may lower the production of sebum that leads to acne, including acne vulgaris, the most common form of acne.

The modified cannabinoid compounds as described herein may be used to treat Alzheimer's disease, and particularly to prevent the development of social recognition deficit in subjects when administered in the early stages of Alzheimer's disease. Other examples of disorders that may be treated by the modified cannabinoid compound as described herein include nausea, vomiting, anorexia, and cachexia. The compounds may produce an appetite-enhancing effect, for example in AIDS patients or individuals with Alzheimer's disease who refuse food.

The modified cannabinoid compounds as described herein may be useful in the treatment of spasticity caused by multiple sclerosis (MS) or spinal cord injury, movement disorders, such as Tourette's syndrome, dystonia, or tardive dyskinesia. MS patients may experience benefits on ataxia and reduction of tremors.

Analgesic properties of the modified cannabinoid compounds may prove beneficial, for example, in the treatment of neuropathic pain due to multiple sclerosis, damage of the brachial plexus and HIV infection, pain in rheumatoid arthritis, cancer pain, headache, menstrual pain, chronic bowel inflammation and neuralgias.

The modified cannabinoid compounds as described herein may be useful in the treatment of asthma. Experiments examining the anti-asthmatic effect of THC or cannabis date mainly from the 1970s, and are all acute studies. The effects of a cannabis cigarette (2% THC) or oral THC (15 mg), respectively, approximately correspond to those obtained with therapeutic doses of common bronchodilator drugs (salbutamol, isoprenaline). Since inhalation of cannabis products may irritate the mucous membranes, oral administration or another alternative delivery system would be preferable. Very few patients developed bronchoconstriction after inhalation of THC.

An improvement of mood in reactive depression has been observed in several clinical studies with THC. There are additional case reports claiming benefit of cannabinoids in other psychiatric symptoms and diseases, such as sleep disorders, anxiety disorders, bipolar disorders, and dysthymia. Various authors have expressed different viewpoints concerning psychiatric syndromes and cannabis. While some emphasize the problems caused by cannabis, others promote the therapeutic possibilities. Quite possibly cannabis products may be either beneficial or harmful, depending on the particular case. The attending physician and the patient should be open to a critical examination of the topic, and a frankness to both possibilities.

In a number of painful syndromes secondary to inflammatory processes (e.g. ulcerative colitis, arthritis), cannabis products may act not only as analgesics but also demonstrate anti-inflammatory potential. For example, some patients employing cannabis report a decrease in their need for steroidal and nonsteroidal anti-inflammatory drugs. Moreover there are some reports of positive effects of cannabis self-medication in allergic conditions. It is as yet unclear whether cannabis products may have relevant effects on causative processes of autoimmune diseases.

There are a number of positive patient reports on medical conditions that cannot be easily assigned to the above categories, such as pruritus, hiccup, ADS (attention deficit syndrome), high blood pressure, tinnitus, chronic fatigue syndrome, restless leg syndrome, and others. Different authors have described several hundred possible indications for cannabis and THC. For example, 2.5 to 5 mg THC were effective in three patients with pruritus due to liver diseases. Another example is the successful treatment of a chronic hiccup that developed after a surgery. No medication was effective, but smoking of a cannabis cigarette completely abolished the symptoms.

Cannabis products often show very good effects in diseases with multiple symptoms that encompassed within the spectrum of THC effects, for example, in painful conditions that have an inflammatory origin (e.g., arthritis), or are accompanied by increased muscle tone (e.g., menstrual cramps, spinal cord injury), or in diseases with nausea and anorexia accompanied by pain, anxiety and depression, respectively (e.g. AIDS, cancer, hepatitis C).

Suitable doses may vary over a wide range depending on a variety of factors including the type and/or severity of the disease or disorder, previous treatments, the general health, age, and/or weight of the individual, the frequency of treatments, the rate of release from the composition, and other diseases present. This dose may vary according to factors such as the disease state, age, and weight of the subject. For example, higher doses may be administered for treatments involving conditions that are at an advanced stage and/or life threatening. Dosage regimens also may be adjusted to provide the optimum therapeutic response.

Pharmaceutical compositions may be formulated together with one or more acceptable pharmaceutical or food grade carriers or excipients. As used herein, the term "acceptable pharmaceutical or food grade carrier or excipient" means a non-toxic, inert solid, semisolid or liquid filler, diluent, encapsulating material or formulation auxiliary of any type. For example, sugars such as lactose, glucose and sucrose; starches such as corn starch and potato starch; cellulose and its derivatives such as sodium carboxymethyl cellulose, ethyl cellulose and cellulose acetate; powdered tragacanth; malt: gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions may be prepared by any suitable technique and is not limited by any particular method for its production. For example, purified cannabinoids can be combined with excipients and a binder, and then granulated. The granulation can be dry-blended with any remaining ingredients, and compressed into a solid form such as a tablet.

Pharmaceutical compositions may be administered by any suitable route. For example, the compositions may be administered orally, parenterally, by inhalation spray, topically, rectally, nasally, buccally, vaginally, via an implanted reservoir, or ingested as a dietary supplement or food. In some embodiments, a composition is provided in an inhaler, which may be actuated to administer a vaporized medium that is inhaled into the lungs. The term parenteral as used herein includes subcutaneous, intracutaneous, intravenous, intramuscular, and intracranial injection or infusion techniques. Most often, the pharmaceutical compositions are readily administered orally and ingested.

Pharmaceutical compositions may contain any conventional non-toxic pharmaceutically-acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

Compositions may contain a modified cannabinoid compound or compounds, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g., a hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. In some aspects, the therapeutic compound may have anti-inflammatory activity, such as a non-steroidal anti-inflammatory drug (NSAID). NSAIDs are a large group of therapeutic compounds with analgesic, anti-inflammatory, and antipyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etoxiolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of a suitable selective COX-2 inhibitors include, without limitation, celecoxib, etoricoxib, firocoxib, lumiracoxib, meloxicam, parecoxib, rofecoxib, and valdecoxib.

A therapeutically effective amount of a therapeutic compound disclosed herein generally is in the range of about 0.001 mg/kg/day to about 100 mg/kg/day. An effective amount may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In some examples, an effective amount of a therapeutic compound may be in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In other examples, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day.

In addition to pharmaceutical compositions, compounds described herein may be formulated as an elixir, a beverage, a chew, a tablet, a lozenge, a gum, or the like. According to another aspect, the pharmaceutical compositions may also be formulated as a pharmaceutically acceptable vehicle such as a capsule, tablet, syrup, lozenge, inhaler, e-cigarette, chewable gum, nasal spray, transdermal patch, liquid, transmucosal vehicle, hydrogel, nanosome, liposome, noisome, nanoparticle, nanosphere, microsphere, microparticle, microemulsion, nanosuspension, or micelle. The compositions may also be formulated, for example, as dietary supplements or nutraceuticals.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While the invention has been described with respect to specific examples, those skilled in the art will appreciate that there are numerous variations and permutations of the above described systems and techniques that fall within the spirit and scope of the invention as set forth in the appended claims.

What is claimed is:

1. A compound having the structure:

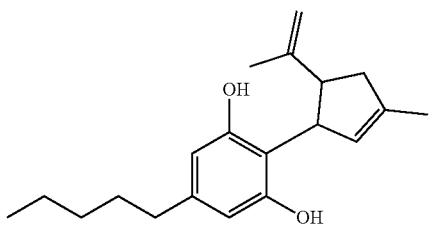 [SMILES: C=C(C)C1CC(C)=CC1c1c(O)cc(CCCCC)cc1O]

or a pharmaceutically acceptable salt thereof.

2. A pharmaceutical composition comprising a compound of claim 1 having the structure:

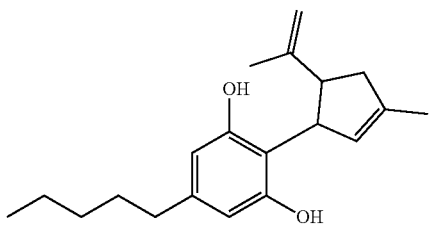 [SMILES: C=C(C)C1CC(C)=CC1c1c(O)cc(CCCCC)cc1O]

or a pharmaceutically acceptable salt thereof, and a pharmaceutically acceptable vehicle therefor.

3. A pharmaceutical composition of claim 2 which contains a racemic mixture of enantiomers having the structures:

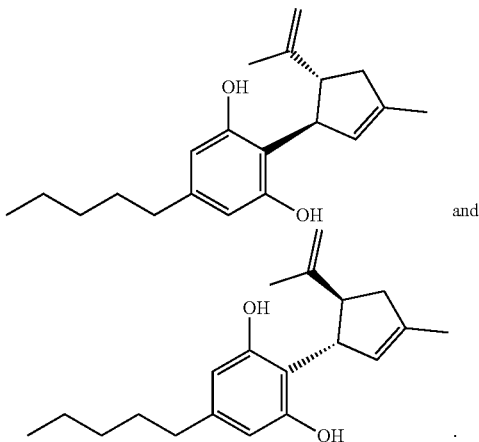

and

4. A pharmaceutical composition of claim 3, wherein the pharmaceutically acceptable vehicle is a capsule, tablet, syrup, lozenge, inhaler, e-cigarette, chewable gum, nasal spray, transdermal patch, liquid, transmucosal vehicle, hydrogel, nanosome, liposome, noisome, nanoparticle, nanosphere, microsphere, microparticle, microemulsion, nanosuspension, or micelle.

5. A pharmaceutical composition of claim 2 which contains an enantiomer, of at least about 99% enantiomeric purity, having the structure:

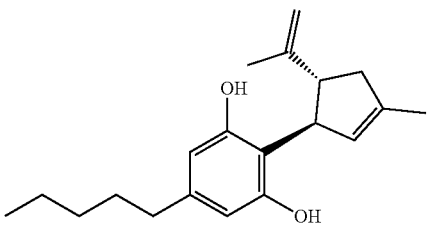

6. A pharmaceutical composition of claim 5, wherein the pharmaceutically acceptable vehicle is a capsule, tablet, syrup, lozenge, inhaler, e-cigarette, chewable gum, nasal spray, transdermal patch, liquid, transmucosal vehicle, hydrogel, nanosome, liposome, noisome, nanoparticle, nanosphere, microsphere, microparticle, microemulsion, nanosuspension, or micelle.

* * * * *